United States Patent [19]

Andrade et al.

[11] Patent Number: 4,680,420

[45] Date of Patent: Jul. 14, 1987

[54] PROCESS FOR THE PRODUCING 2,5-DIMETHOXYTETRAHYDROFURAN AND 2,5-DIETHOXYTETRAHYDROFURAN

[75] Inventors: Juan Andrade, Ridgewood, N.J.; Günter Prescher, Hanau, Fed. Rep. of Germany

[73] Assignee: Degussa Aktiengesellschaft, Frankfurt, Fed. Rep. of Germany

[21] Appl. No.: 936,296

[22] Filed: Dec. 1, 1986

[30] Foreign Application Priority Data

Dec. 13, 1985 [DE] Fed. Rep. of Germany ....... 3544046

[51] Int. Cl.$^4$ .......................................... C07D 307/20
[52] U.S. Cl. .................................................. 549/476
[58] Field of Search ......................................... 549/476

[56] References Cited

U.S. PATENT DOCUMENTS 2,920,081  1/1960  Privette et al. .................... 549/476

Primary Examiner—Richard L. Raymond
Attorney, Agent, or Firm—Beveridge, DeGrandi & Weilacher

[57] ABSTRACT

A process is described for producing 2,5-dimethoxytetrahydrofuran and 2,5-diethoxytetrahydrofuran by treating 4,4-dimethoxy-1-butanal and 4,4-diethoxy-1-butanal with a strongly acidic ion exchange resin at a temperature of between 0° and 70° C.

7 Claims, No Drawings

PROCESS FOR THE PRODUCING 2,5-DIMETHOXYTETRAHYDROFURAN AND 2,5-DIETHOXYTETRAHYDROFURAN

The invention pertains to a process for producing 2,5-dimethoxytetrahydrofuran and 2,5-diethoxytetrahydrofuran. It is known to produce these compounds by treating 1,5,9-cyclododecatriene with ozone and methanol and converting the resulting ozonization product by hydration and subsequent distillation to form 2,5-dimethoxytetrahydrofuran and 2,5-diethoxytetrahydrofuran, Japanese patent No. 19930, 1971 (C.A. 1971, vol. 75;98166e).

A disadvantage of this known process resides in the fact that a mixture is obtained which consists of approximately 60% succinaldehydtetramethyl- or tetraethylacetal and 40% 2,5-dimethoxytetrahydrofuran or 2,5-diethoxytetrahydrofuran.

It is also known to chlorinate tetrahydrofuran and convert the resulting 2,5-dichlorotetrahydrofuran with sodium methylate or sodium ethylate to form the desired dialkoxytetrahydrofurans; East German patent No. 25656.

A disadvantage of this known process is the poor yield from the chlorination step.

It is further known to obtain 2,5-dialkoxytetrahydrofurans starting with furan. To carry this out, furan is reacted with bromine and the corresponding alcohol and the resulting product is hydrated to form 2,5-dialkoxytetrahydrofuran; J. Am. Chem. Soc., 72, 869 (1950).

According to the present invention, there is provided a simple process for producing the desired compounds by treating 4,4-dimethoxy-1-butanal or 4,4-diethoxy-1-butanal with a strongly acidic ion exchange resin at a temperature of between 0 and 70° C.

Preferably, the reaction with the ion exchange resin is carried out at a temperature of between 20 and 60° C.

In a preferred aspect of the invention, 0.001–0.1 part by weight of the strongly acidic ion exchange resin is used for each part by weight of the butanal.

The 4,4-dialkoxybutanals used as starting material can be obtained by methods known in the art, for example, the process described in DE-OS No. 3,403,427; the entire disclosure of which is relied on and incorporated by reference. In this known process, acrolein is converted to a 3,3-dialkoxy-1-propene, and this product is hydroformylated in the presence of hydridotris-triphenylphosphinerhodium carbonyl, as well as triphenylphosphite as catalysts.

The appropriate strongly acidic ion exchange resins are widely known in the art and preferably consist of styrene-divinylbenzene mixed polymerizates, which carry sulfo-groups as functional components. These are usually referred to as sulfonated copolymers of styrene and divinylbenzene. See Kirk-Othmer, Encyclopedia of Chemical Technology, Vol. 9, pp. 678–697, 3rd Edition, relied on herein. Commercially available examples are Dowex MSC-1 and Amberlite IR-200C. Any suitable acidic ion exchange resin can be used for purposes of the invention. Generally, the ion exchange resins are in finely divided form, as granules, beads or pellets.

The process of the invention can be carried out in such a way that, for example, the 4,4-dialkoxy-1-butanal is stirred in the presence of the ion exchange resin for a fairly long time at a temperature of between 20° and 60° C. Stirring times of about 1 hour to 5 hours are illustrative as may be seen from the examples herein. Once the reaction is completed, the mixture is processed in a suitable way to recover the product. This can be carried out, for example, by filtering off the ion exchange resin and then subjecting the reaction mixture to fractional distillation.

The invention is illustrated and described in greater detail by the following examples:

EXAMPLE 1

50 g (0.38 mol) of 4,4-dimethoxy-1-butanal is mixed with 5 g of a strongly acidic ion exchange resin (Dowex MSC-1) and stirred for three hours at 60° C. As a result, 74% of the butanal that was charged into the reaction vessel is reacted. Subsequently, the ion exchange resin is filtered off and the reaction mixture is distilled under reduced pressure. At an overhead temperature of approximately 80° C. (100 mbar), 31.3 g of 2,5-dimethoxytetrahydrofuran is distilled off. 97.6% of the product consists of the cis- and trans-isomers of the desired compound. The yield, relative to the reacted 4,4-dimethoxybutanal, is therefor 82.6%.

EXAMPLE 2

32 g (0.2 mol) of 4,4-diethoxy-1-butanal is mixed with 1.0 g of strongly acidic ion exchange resin (Amberlite IR-200C) and is stirred for two hours at 40° C. As a result, 86% of the butanal that was charged into the reaction vessel has been reacted. Subsequently, the ion exchange resin is filtered off and the filtrate is distilled under reduced pressure. At an overhead temperature of 64°–67° C., 24.7 g of 2,5-diethoxytetrahydrofuran is distilled off. The product is a mixture of cis- and trans-isomers and amounts to 96.6%. The yield, relative to the butanal used, is 86.7%.

EXAMPLE 3

The procedure is the same as in Example 1, but a mixture of 132 g (1.0 mol) of 4,4-dimethoxy-1-butanal and 2.6 g of ion exchange resin (Amberlite IR-200C) are used and the mixture is stirred for 1.5 hours at 50° C. The conversion is 94%. 98% of the product consists of the cis- and trans-isomers of 2,5-dimethoxytetrahydrofuran. The compound boils at 144°–147° C. The yield, relative to the reacted butanal, is 95.2%.

EXAMPLE 4

The procedure is the same as in Example 2, but a mixture of 80 g (0.5 mol) of 4,4-diethoxy-1-butanal and 4 g of ion exchange resin (Dowex MSC-1) are used and stirred for four hours at 30° C. The conversion is 82%. After the ion exchange resin is separated, a product is distilled off at 63°–65° C. (20 mbar), 97.5% of which consists of the cis- and trans-isomers of 2,5-diethoxytetrahydrofuran. The yield, relative to the butanal used, is 91%.

Further variations and modifications of the invention will be apparent to those skilled in the art from the foregoing and are intended to be encompassed by the claims appended hereto.

We claim:

1. A process for producing 2,5-dimethoxytetrahydrofuran and 2,5-diethoxytetrahydrofuran, comprising reacting 4,4-dimethoxy-1-butanal or 4,4-diethoxy-1-butanal with a strongly acidic ion exchange resin at a temperature of between 0° and 70° C.

2. The process according to claim 1, wherein 0.001–0.1 part by weight of the strongly acidic ion exchange resin is used for each part by weight of the butanal.

3. The process according to claim 1, wherein the reaction is carried out at a temperature of between 20° and 60° C.

4. The process according to claim 1, wherein the ion exchange resin is a sulfonated copolymer of styrene and divinylbenzene.

5. The process according to claim 4, wherein the resin is in finely divided form.

6. The process according to claim 1, further comprising filtering off the ion exchange resin after the reaction and then distilling off the 2,5-dimethoxytetrahydrofuran and 2,5-diethoxytetrahydrofuran as the recovered product.

7. The process according to claim 6, wherein the recovered product contains the cis- and trans-isomers thereof.

* * * * *